United States Patent [19]

Olsen

[11] 4,211,323
[45] Jul. 8, 1980

[54] DISPOSABLE DIAGNOSTIC SWAB HAVING A STORED CULTURE MEDIUM

[75] Inventor: C. Eric Olsen, Ventura, Calif.

[73] Assignee: California Medical Developments, Inc., Ventura, Calif.

[21] Appl. No.: 965,564

[22] Filed: Dec. 1, 1978

[51] Int. Cl.$^2$ .................... A61B 10/00; A61B 25/00
[52] U.S. Cl. ............................. 206/210; 206/219; 206/363; 206/456; 128/269
[58] Field of Search ............... 206/363, 364, 210, 219, 206/569, 570, 571, 438, 456; 128/2 W, 269, 272

[56] References Cited

U.S. PATENT DOCUMENTS

| | | | |
|---|---|---|---|
| 3,308,039 | 3/1967 | Nelson | 128/2 W |
| 3,648,704 | 3/1972 | Jackson | 206/364 X |
| 3,651,926 | 3/1972 | Elfast, Jr. | 206/456 |
| 3,835,834 | 9/1974 | Brown et al. | 128/269 X |
| 3,913,562 | 10/1975 | Moore et al. | 206/363 X |
| 3,967,728 | 7/1976 | Gordon et al. | 206/364 |
| 4,014,748 | 3/1977 | Spinner et al. | 128/2 W X |

Primary Examiner—Joseph Man-Fu Moy
Attorney, Agent, or Firm—Jack C. Munro

[57] ABSTRACT

A disposable diagnostic swab assembly which takes the form of an elongated tubular member having an internal chamber which is permanently closed at the inner end and is openable at the outer end by the removal of a cap. A culture medium containing breakable pouch is located within the internal chamber at the inner end. An elongated swab is attached to the cap with the tip of the swab being located directly adjacent the pouch. The pouch is to be breakable by applying localized pressure upon the tubular member in the area of the pouch which causes the culture medium to saturate the tip of the swab. A glass slide section may also be attached to the tubular member with access to the glass slide being permitted to facilitate usage thereof.

2 Claims, 5 Drawing Figures

DISPOSABLE DIAGNOSTIC SWAB HAVING A STORED CULTURE MEDIUM

BACKGROUND OF THE INVENTION

This invention relates to a swabbing apparatus which is to be used by physicians and technicians for collecting a culture from various areas of the patient's body, such as the ears, nose and throat, and for keeping the culture moist and alive for a period of time after it is collected.

The swabbing units of the prior art customarily comprise an absorbent swab upon which the culture is collected by swabbing the particular body area, and a separate container in which the swab is inserted and kept moist so that the collected culture will be in an alive condition when subsequently tested.

It has been common in the past to employ the use of an individual disposable container which contains a sterile swab (prior to use) and a quantity of culture medium. The swab after use is inserted back into the container and the culture medium is caused to come into contact with the tip of the swab. The swab is then marked according to the particular patient and then transmitted to a laboratory where it is then removed and processed according to normal practice. The fact that the tip of the swab has remained moist due to the culture medium is to insure the growth of the culture during the transporting of it to the laboratory. Also, because the swab has been supported within a container, which is completely closed, contamination by foreign organism is prevented. This means that the infection grown on the tip of the swab is definitely attributable to the patient. Once the individual type of swab has been used, such is then discarded to not insure reuse.

The individual swabbing devices of the prior art have been only able to contain a minimal amount of culture medium. At certain times it would be desirable to contain a greater quantity of culture medium due to the type of organism for which the test is being performed. Additionally, there has not been any structure which is to confine the culture medium directly to the tip of the swab and at times the culture medium will be conducted along the length of the swab which causes the tip of the swab to dry out. The drying out of the tip of the swab can cause complete destruction of the organisms which were located on the tip of the swab.

Additionally, in the past it has not been known to provide a glass slide section in conjunction with the swabbing unit. At times it may be desirable to smear the tip of the swab on a glass slide prior to insertion within the swabbing unit. This means that the laboratory personnel would have not only the availability of growing the culture but also the availability of observing the organisms on the glass slide by a microscrope.

SUMMARY OF THE INVENTION

The structure of this invention relates to the inclusion of a disposable, inexpensive swabbing unit which has been summarily described in the Abstract of the Disclosure and reference is to be had thereto.

A primary objective of this invention is to construct a swabbing unit which comprises a disposable tube which is to contain both a swab and a sealed quantity of medium which can be brought together when needed.

Another objective of this invention is to provide a disposable culture device that insures complete sterility in that even the swab is never touched by the operator and the swab is maintained in a completely confined state after use.

Another objective of this invention is to provide not only a culture producing swab section but also to provide for a glass slide which is to be adapted to receive smears of the culture at the time the culture was taken.

DETAILED DESCRIPTION OF THE SHOWN EMBODIMENT

Figure 1:
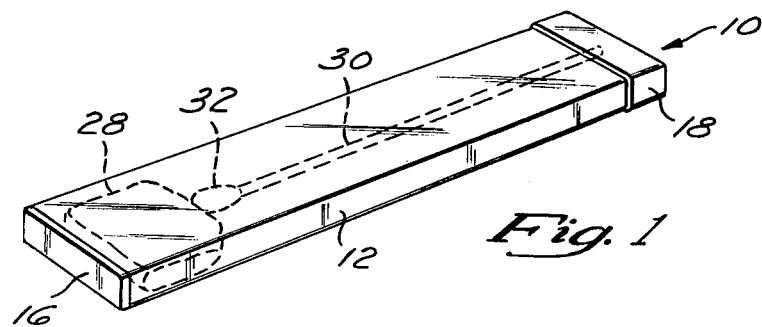
FIG. 1 is an isometric view of the disposable diagnostic swab assembly of this invention.
Figure 2:
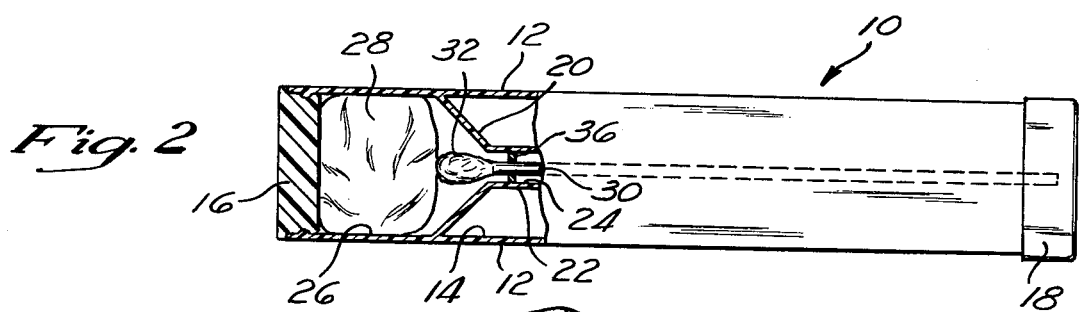
FIG. 2 is a top view, partly in cross-section, of the disposable diagnostic swab assembly shown in FIG. 1.

Referring particularly to the drawing there is shown a disposable diagnostic swabbing device 10 of this invention which is composed primarily of an elongated tubular plastic member 12 having an internal chamber 14. The internal chamber 14 has an inner end which is permanently closed by means of a plug 16. The outer end of the chamber 14 is normally closed by a removable cap 18.

Located within the internal chamber 14 is a pair of wall members 20 and 22. The wall members 20 and 22 are located in a spaced apart manner and form an elongated narrow chamber 24. Adjacent the plug 16 and located forward of the chamber 24 is an enlarged chamber 26 which forms a part of the chamber 14.

Figure 3:
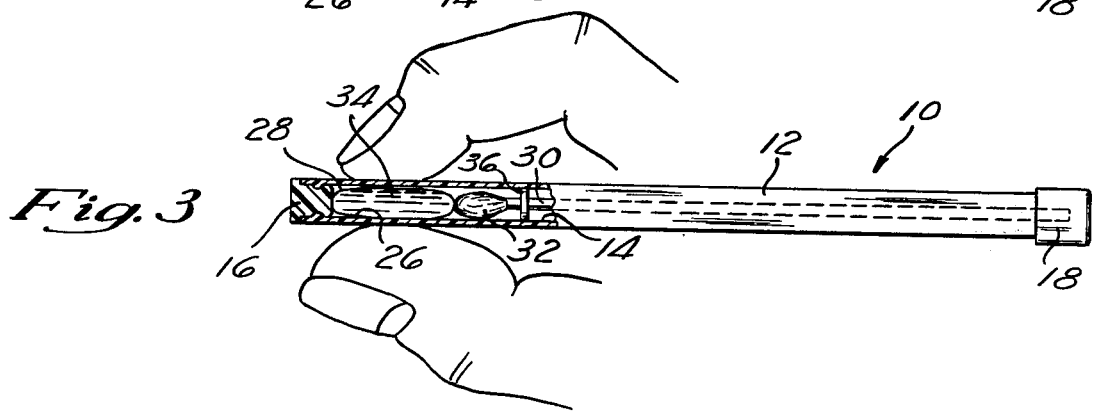
FIG. 3 is a side, partially cross-sectional view similar to FIG. 2 but showing the procedure for breaking the pouch which contains the culture medium.

Sealed within a thin, flexible walled pouch 28 is a culture medium. This culture medium will usually take the form of distilled water, saline solution or other non-reactive liquid which is to provide an environment in which the culture can live but which does not affect the culture. The material of construction of the pouch 28 is to be readily breakable by applying localized pressure such is depicted generally within FIG. 3 of the drawing. The localized pressure, though able to break the pouch 28, does not break the wall of the elongated member 12.

Attached to the inside of the cap 18 is a swab 30. The swab 30 has an absorbent tip (usually cotton) 32. The swab 30 is to extend through the chamber 24 with the tip 32 being located within the enlarged chamber 26 directly adjacent the pouch 28.

Once the pouch 28 is broken, it is desirable to keep the culture medium 34 confined within the enlarged chamber 26 and not permit such to be conducted into the chamber 24. In order to prevent this, a flexible sealing disc 36 is attached to the swab 30 directly adjacent the tip 32. The periphery of the disc 36 is to be in contact with the sidewall of the chamber 24. The disc 36 does not hinder the insertion or removal of the swab 30.

It may be desirable to integrally connect with the swabbing unit 10 a glass slide section 38. The glass slide section is to include a glass slide 40 which is to be smeared with a portion of the obtained culture. Examination of the glass slide 40 under a microscope by a laboratory technician may provide desired information concerning the obtained culture. Previous to this invention there has been no known combining of a glass slide section within an individual swabbing unit.

The glass slide section 38 includes an outer member 42 and a inner member 44. The outer member 42 is integrally connected by a first webb 46 to the tubular member 12. The inner member 44 is also integrally connected by a web 48 to the housing 12. The webs 46 and 48 include large cut-out areas in order to facilitate separating of the inner member 44 from the outer member 42 so as to gain acess to the slide 40. It is to be noted that the slide 40 rests upon protuberances 50 provided on the inside surfaces of both the members 42 and 44.

In actual practice the glass slide 40 will be retained in a sterile condition prior to use as also the tip 32 of the swab 30. The operator is to remove the swab 30 from the tubular member 12 and rub it upon the particular area of the patient's body so as to pick up the organisms in that particular area. The operator then may reinsert the swab back into the tubular member 12 thereby again closing the chamber 14 and then cause breaking of the pouch 28 and release of the meduim 34 to come in contact with the tip 32 to the swab 30. The swabbing unit is then to be transmitted to an appropriate laboratory for examination.

Figure 4:
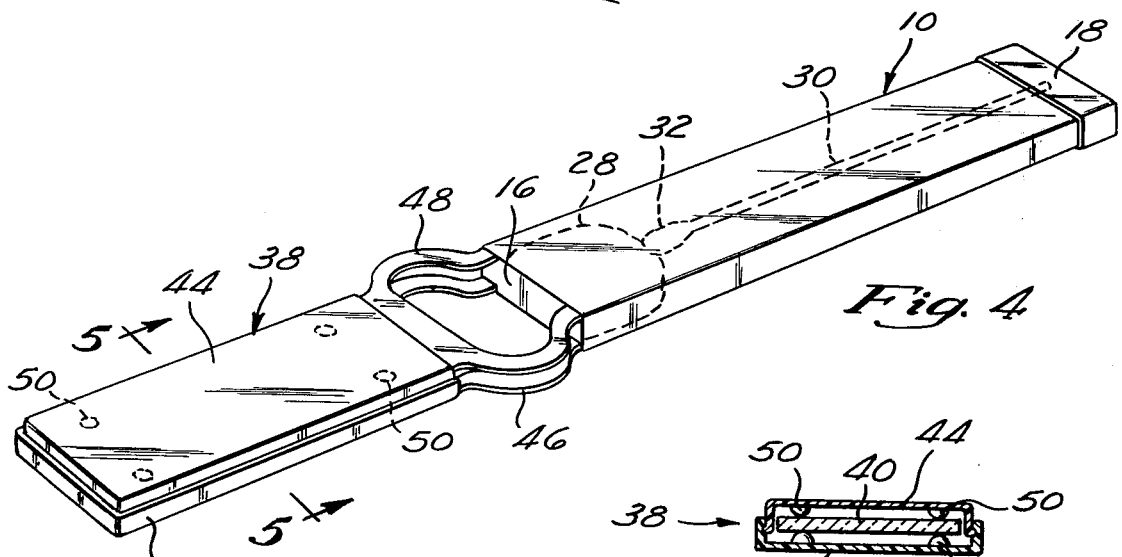
FIG. 4 is an isometric view of the disposable diagnostic swab assembly of this invention showing the addition of a glass slide section.
Figure 5:
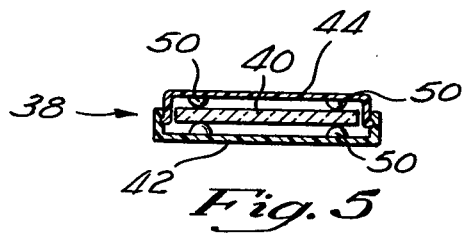
FIG. 5 is a cross-sectional view through the glass slide section of FIG. 4 taken along line 5—5 of FIG. 4.

When using the embodiments of this invention shown within FIGS. 4 and 5, the operator also has the option of separating the glass slide members 42 and 44 which permits access to the glass slide 40. The operator is to normally take this swab 30 and locate a smear on the surface of the glass slide 40 prior to reinsertion of the swab 30 back into the tubular member 12. After the glass slide 40 has been smeared, the members 42 and 44 are snapped back together to form a sealed, closed unit and prevent contamination of the slide 40 by any foreign material. The entire unit of FIG. 4 is then transmitted to an appropriate laboratory for examination.

What is claimed is:

1. A disposable diagnostic swab having a stored culture medium comprising:

an elongated tubular member having an internal chamber, said chamber having an inner end and an outer end, said inner end being permanently closed, said outer end being normally closed by a removable cap, the wall of said elongated tubular member being substantially rigid but readily deflectable upon incurring a small amount of localized manual pressure;

a pouch completely enclosing a quantity of culture medium, the wall of said pouch being constructed of a thin readily breakable material upon incurring a small amount of manual pressure, said pouch being located within said internal chamber at said inner end;

a swab having a tip and and an aft end interconnected by an elongated swab body, said swab located within said internal chamber with said aft end located at said outer end and said tip located directly adjacent said pouch, whereby said pouch may be ruptured causing immersion of said tip by said culture medium;

said internal chamber including an internal separating wall assembly to closely confine said swab, a portion of said internal separating wall assembly cooperating with said tubular member to substantially totally enclose said pouch, said internal separating wall assembly including a pair of spaced-apart wall members with each said wall member being substantially parallel to said swab body, said swab body being located between said wall members; and a flexible sealing member mounted on said swab adjacent said tip, said flexible sealing member to be in physical, liquid tight contact with said wall members which results in totally enclosing said pouch, said flexible sealing member to prevent the flow of culture medium longitudinally along said swab and therefore insure that said culture medium is confined to said tip of said swab.

2. The disposable diagnostic swab as defined in claim 1 including:

a glass slide section being attached to said elongated tubular member, said glass slide section to include a sterilized glass slide to be normally located within the housing of said glass slide section, said housing being openable to gain access to said glass slide to thereby facilitate usage thereof.

* * * * *